United States Patent
Doerrer et al.

[11] Patent Number: 5,889,880
[45] Date of Patent: *Mar. 30, 1999

[54] INTERACTIVE AUTOMATED CYTOLOGY METHOD INCORPORATING BOTH MANUAL AND AUTOMATIC DETERMINATIONS

[75] Inventors: Rainer Hermann Doerrer, Greensboro; Jochen Ernst Fischer, Elon College; Ernest Arthur Knesel, Greensboro, all of N.C.; Thanh Van Nguyen, Palo Alto, Calif.

[73] Assignee: Autocyte, Inc., Burlington, N.C.

[*] Notice: The term of this patent shall not extend beyond the expiration date of Pat. No. 5,677,966.

[21] Appl. No.: 869,699

[22] Filed: Jun. 5, 1997

Related U.S. Application Data

[63] Continuation of Ser. No. 483,637, Jun. 7, 1995, Pat. No. 5,677,966.

[51] Int. Cl.$^6$ ........................................... G06K 9/00
[52] U.S. Cl. ................................. 382/128; 382/133
[58] Field of Search ........................ 382/128, 133, 382/134, 168, 209, 309, 311

[56] References Cited

U.S. PATENT DOCUMENTS

| | | |
|---|---|---|
| 4,523,278 | 6/1985 | Reinhardt et al. ................. 364/413 |
| 4,612,614 | 9/1986 | Deindoerfer et al. ............... 364/415 |
| 4,965,725 | 10/1990 | Ruetenberg ..................... 364/413.1 |
| 5,031,099 | 7/1991 | Kettler ........................ 364/413.08 |
| 5,072,382 | 12/1991 | Kamentsky ..................... 364/413.08 |
| 5,073,857 | 12/1991 | Peters et al. .................... 364/413.1 |
| 5,235,522 | 8/1993 | Bacus ................................ 382/133 |
| 5,257,182 | 10/1993 | Luck et al. ..................... 364/413.1 |
| 5,287,272 | 2/1994 | Rutenberg et al. .............. 364/413.09 |
| 5,333,207 | 7/1994 | Rutenberg ........................... 382/6 |
| 5,487,112 | 1/1996 | Zygourakis et al. ................ 382/133 |
| 5,677,966 | 10/1997 | Doerrer et al. ..................... 382/128 |

FOREIGN PATENT DOCUMENTS

| | | |
|---|---|---|
| 014 857 | 2/1985 | European Pat. Off. . |
| 557 871 | 2/1993 | European Pat. Off. . |
| 91/15826 | 10/1991 | WIPO . |
| 92/13308 | 8/1992 | WIPO . |
| 93/16436 | 8/1993 | WIPO . |

OTHER PUBLICATIONS

AutoCyte Interactive Automated Cytology Brochure, Roche Image Analysis Systems, 1992 Roche Biomedical Laboratories, Inc.

Automated Cervical Cancer Screening, An International Perspective, Oct. 17–19, 1991, Hyatt Regency Tech Center, Denver, Colorado.

Automated Cervical Cancer Screening, Second Annual International Symposium, Oct. 29–31, 1992, Georgia International Convention.

(List continued on next page.)

*Primary Examiner*—Phuoc Tran
*Attorney, Agent, or Firm*—Alston & Bird LLP

[57] ABSTRACT

An automated interactive cytology system provides expedited handling of samples, minimizing false negatives, while not substantially increasing the number false positives. A computerized system identifies and displays the cells which are of greatest interest to the cytologist. The system then processes this information on all cells identified to classify the slide as normal, abnormal, or questionable based on a statistical analysis of cells meeting given criteria. Before displaying the results of the statistical analysis, a cytologist reviews the cells which the computer has determined to be most significant. It is only then after the cytologist has determined whether the cells are positive, negative, or questionable, that the determination is inputted into the automated system. The automated system then compares the cytologist's analysis with its own statistical analysis. Based on the two opinions, the cytologist determines how to advise a doctor regarding the sample.

45 Claims, 5 Drawing Sheets

OTHER PUBLICATIONS

Al et al., *The Journal of Histochemistry and Cytochemistry,* vol. 27(1):629–634 (1979).

Bengtsson et al., *The Journal of Histochemistry and Cytochemistry,* vol. 27(1):621–628 (1979).

Gahm et al., *Micron and Microscopica Acta.,* vol. 21(1/2):29–55 (1990).

Ploem et al., *Clinical Cytometry and Histometry,* "Leytas—A Cytology Screening System Using the New Modular Image Analysis Computer (MIAC) From Leitz," pp. 25–35 (1987).

Ploem et al., *The Journal of Histochemistry and Cytochemistry,* vol. 27(1):136–143 (1979).

Tanaka et al., *The International Academy of Cytology Analytical and quantitative Cytology,* pp. 122–126, Manual of Cytotech, 3rd, Ed., Government published 1965, p. 14–1.

Gahm, T., *Cesar Zytoanalysator,* I–IX, 1–152, and i–iii, Hannover (1989).

INTERACTIVE AUTOMATED CYTOLOGY METHOD INCORPORATING BOTH MANUAL AND AUTOMATIC DETERMINATIONS

This application is a continuation of application Ser. No. 08/483,637 filed 7 Jun. 1995, now U.S. Pat. No. 5,677,966.

BACKGROUND OF THE INVENTION

1. Field

The invention relates to the field of automated cytology, and in particular to an interactive system of automated cytology in which a cytotechnologist or cytopathologist interacts with an automated cytology screening system to markedly increase accuracy.

2. Description

Cytotechnologists and cytopathologists are human, and thus subject to human frailties. Among these frailties are drowsiness, inattentiveness, illness, stress, boredom, and fatigue. Moreover, current cytology practice involves a certain amount of subjectivity. By contrast, a computer is devoid of human frailties and totally objective. Accordingly, there has long been sought an automated, computerized system for cytological analysis.

Presently, several computerized cytology systems are being introduced into the market place. Cytyc Corporation has been developing its CDS-1000™ cytology workstation in which a computer system identifies cells having the highest potential for being abnormal, representative normal cells for the comparison, and clusters of cells which may be of interest to the system operator. Such a system provides the cytotechnologist or cytopathologist ("cytologist") with a narrowed field of cells for review, but generates no machine interpretation as to specimen normality or abnormality.

NeoPath, Inc. has been developing its AutoPap™ 300 system for automatic screening of conventional Papanicolaou slide smears. This automatic analysis system scans multiple smears and classifies each smear either as normal or requiring review. Only samples classified as needing further review are to be reviewed by a cytologist and no cell images are selected for display.

On the other hand, automated computer systems also have their drawback. Although a computer system adds uniformity based on its statistical analysis approach, there is no practical way for the computer to interpret abnormality based on the presence of only a few abnormal cells. Thus, many systems do not rely on the computer to interpret the normality or abnormality of the cells. Neuromedical Systems, Inc. has been developing its Papnet® system designed with the philosophy that the actual evaluation of the cells and interpretation of the case are left to the cytologist reviewing the case, since the task is both highly complex and subjective. The cytologist reviews each case on a high-resolution, full-color monitor having images displayed in a grid-like manner. Here again there is no computer interpretation of the specific cases.

Moreover, automated cytological specimen classification systems and methods, have been described in U.S. Pat. No. 4,965,725, issued Oct. 23, 1990 to Rutenberg, international publication number WO 91/15826, published Oct. 17, 1991 (claiming priority of U.S. patent application Ser. No. 179,060, filed Apr. 8, 1988, Ser. No. 420,105, filed Oct. 11, 1989, and Ser. No. 425,665, filed Oct. 23, 1989), and international publication number WO 92/13308, published Aug. 6, 1992, and European Patent Publication No. 0 557 871, published Sep. 1. 1993. The contents of each of the above-identified applications, publications and patents, are incorporated herein by reference. Additionally, European Patent Publication No. 0 014 857, published May 2, 1985, describes a method for automatically marking cells and displaying them on a television screen. The contents of this publication are also herein incorporated by reference.

Systems currently under development have sought either to totally automate the cytology system, and thus eliminate the role of the cytologist, or to generate a system merely for preselecting representative cells to be viewed by a cytologist. Until development of the present invention, no attempt has been made to combine cell preselection and cytotechnologist review with an independent machine interpretation, an interactive system in which the cytologist and automated system interact to minimize false negatives, without substantially increasing the occurrence of false positives.

SUMMARY OF THE INVENTION

An interactive method evaluates objects of interest in a sample for a given criterion using a computer-assisted system and an operator, such as for cytology screening. This method comprises (a) the system scanning the sample into an automated scanning device and generating scan data corresponding to the sample, (b) the system identifying objects of interest from the scan data by comparing the scan data with previously inputted data corresponding to a first predetermined set characteristics, (c) the system generating a gallery of the objects of interest, the gallery including the objects of interest which exhibit the first predetermined set of characteristics, (d) the system computing occurrence of the objects and determining whether the occurrence meets a predetermined threshold, (e) the operator viewing the gallery to independently determine whether any of the objects of interest exhibit a second predetermined set of characteristics without knowing the system's determination, (f) the operator inputting the determination of whether the objects of interest exhibit the second predetermined set of characteristics, (g) then the system displaying to the operator the determination of whether the occurrence meets the predetermined threshold, and (h) comparing the operator's determination with the system's determination, agreement indicating that the given criterion has been met.

It is an object of this invention to decrease the rate of false negative diagnoses while not substantially increasing the rate of false positive diagnoses. This object is fulfilled by the features described above. By decreasing the rate of false negative diagnosis, patients are afforded an improved opportunity for early treatment. A further object of this invention is to expedite the cytology process and to reduce per slide cytologist time. This object is met through the generation of a cell gallery which enables a cytologists to review a limited number of cells most likely to contain abnormalities, thus vastly reducing the time required to review a slide typically containing greater than 20,000 cells.

DETAILED DESCRIPTION OF THE INVENTION

The subject invention will now be described in terms of its preferred embodiments. These embodiments are set forth to aid in the understanding of the subject invention, but are not to be construed as limiting.

Figure 4:
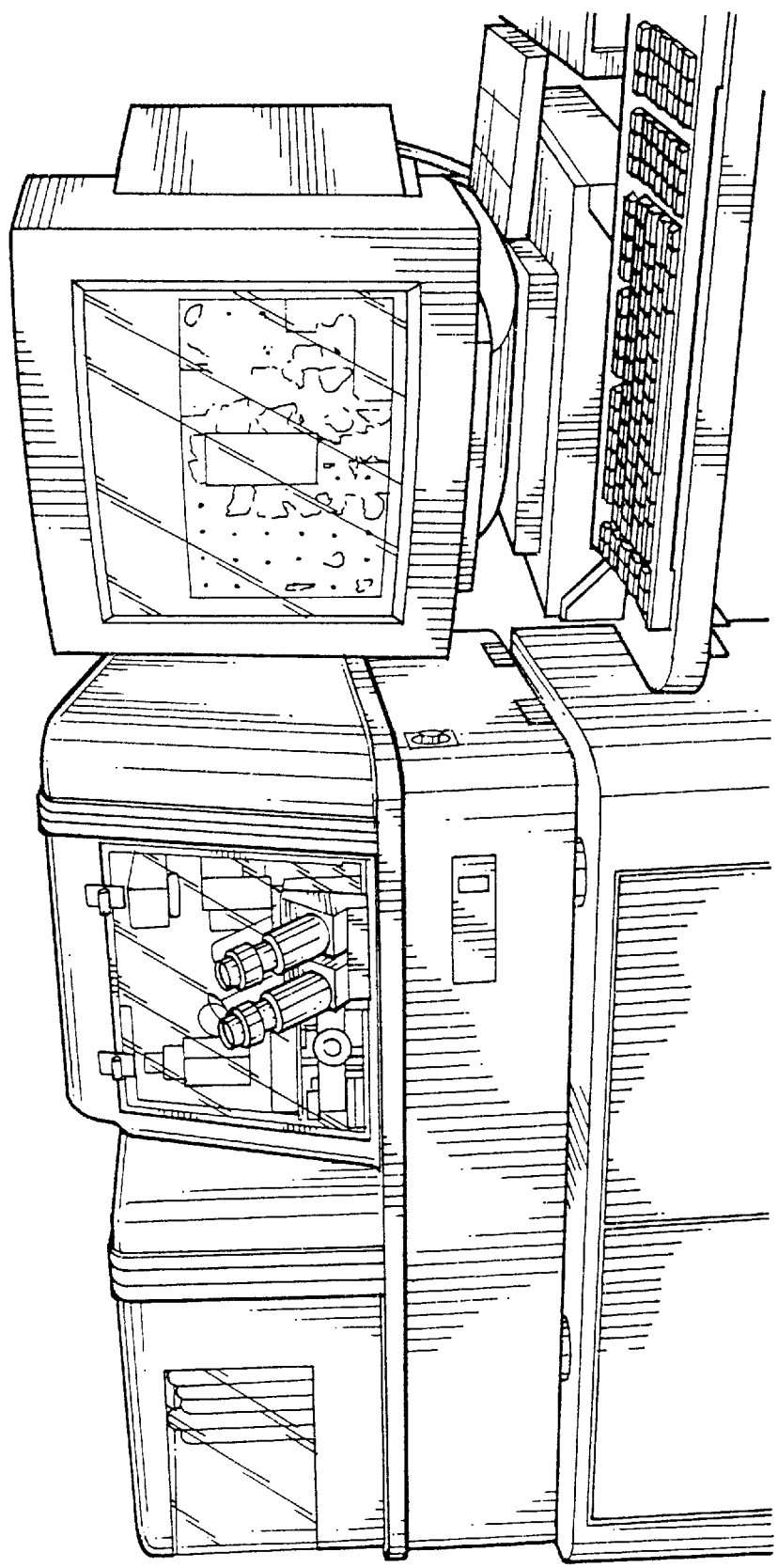
FIG. 4 is a perspective view of one embodiment of the subject system.

The invention relates to an integrated system which combines a cytologist (the term "cytologist" as used herein refers to a cytotechnologist, cytopathologist, or other person who may review a cytology slide) and an automated specimen evaluation system. The automated specimen evaluation system is to be sold under the Autocyte trademark and FIG. 4 illustrates one embodiment of this system.

The automated specimen evaluation system generally comprises (a) means for scanning the sample and generating scan data, (b) means for identifying objects of interest from the scan data by comparing the scan data with previously inputted data corresponding to a first predetermined set of characteristic, (c) means for generating a gallery of the objects, the gallery including the objects which exhibit the first predetermined characteristic, (d) means for computing occurrence of the objects of interest and determining whether the occurrence meets a predetermined threshold, (e) means for displaying the gallery to an operator, (f) means for inputting the operator's determination of whether the objects of interest exhibit a second predetermined set of characteristics, and (g) means for displaying the determination of whether the occurrence meets the predetermined threshold.

The first step of any cell review process is obtaining cells to be reviewed. Any cell type may be analyzed using the subject method and system, although it currently appears that gynecological specimens presently analyzed as pap smears will be the first cells suitable for commercial applications. Although it is envisioned that numerous cell preparations, such as smears, blots, etc., and all cell types will eventually be analyzable by the subject invention, presently, cellular monolayers of cervical scrapings have proven suitable for analysis. Methods for disaggregating these cells, preparing the disaggregated cells as a monolayer, and staining the cells using a modified Papanicolaou stain, have been described in U.S. patent application Ser. Nos. 07/953,035, 07/953,036, and 07/953,037, each filed Sep. 29, 1992, and Ser. Nos. 08/112,001, 08/112,002 and 08/112,003, each filed Aug. 30, 1993. The contents of each of the above are herein incorporated by reference.

The automated specimen evaluation system preferably includes an automated microscope and slide handler. Slides are bar code labeled and loaded into cassettes that hold 40 slides each. These cassettes are in turn loaded onto a carousel that accommodates 10 cassettes. Slides are automatically removed and placed onto an automatic stage after the bar codes have been read. All system controls and cell classification are controlled by a multiprocessor RISC Computer, e.g. a SUN 4 processor. The microscope currently used is a ZEISS inverted microscope. Of course other brandname components may be used in the practice of the invention. Tradenames have been provided merely for guidance to those individuals skilled in the art.

Numerous systems may be used for holding multiple slides for use in automated reviewing systems. These systems can be carousel based, or placed in cassettes or other type array. For the purposes of the present invention, any slide delivery system may be used. The bar code may be read simultaneously or sequentially with the slide. Although currently developed hardware holds up to 400 slides, more extensive hardware can be developed by one skilled in the art.

Slides are removed from the hardware and placed one at a time under a microscope having an automatic positioning and focusing device. This device preferably has means for correlating the position of any given cell, so that the cell can be located at a later time in the event manual review by the cytologist is required.

Figure 3:
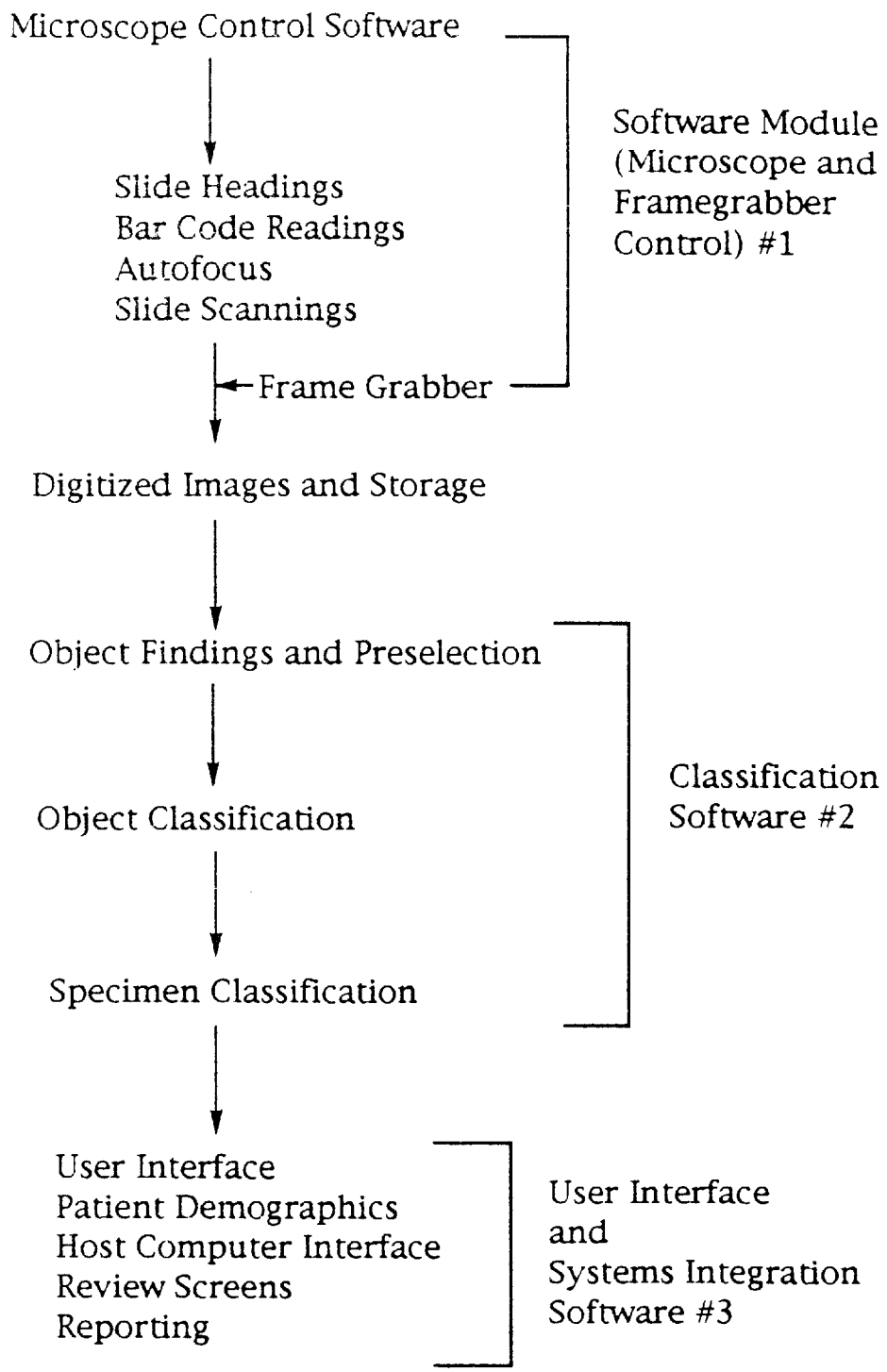
FIG. 3 is an expanded flow chart depicting an embodiment of the subject interactive process and illustrating which elements are controlled by each software system.

To achieve and coordinate the described activities, three major software components have been developed (see FIG. 3). The first software component, the microscope and frame grabber control program, controls the microscope and frame grabber hardware. It regulates and/or controls loading the slides, moving the scanning stage, focusing on cells, and storing digitized images for use by the other software modules. Although a digitalized data storage and retrieval are described, it is within the expertise of the skilled artisan to utilize analog components, and/or analog/digital converters.

The second software component is for cell classification and specimen evaluation. This portion of the system software regulates and/or controls all procedures ranging from reviewing the microscopic images to generating the gallery of significant cells to the final specimen evaluation. This second software component accomplishes three tasks: The first task is object finding and pre-selection of cells and other significant objects. In preselection, insignificant objects are rejected by a course classification. The second task is object classification. All objects identified in the first task are classified and those deemed most significant are inserted into the cell gallery. The third task is specimen, classification. In this task, all objects are classified and cell populations are statistically analyzed to generate a specimen classification. This is an independent machine classification.

The third software component is the user interface and control module. This module communicates with the human user, and controls all parts of the software, such as the hardware control, classification and evaluation. It also stores the results and scanned images on the disk after completion of the slide scanning.

The three software components presently used can be developed by one skilled in the art based on software packages that are currently known. Software of necessity needs to be adapted for particular applications, and such adaptation is within the skill of the artisan in this field.

Figure 1:
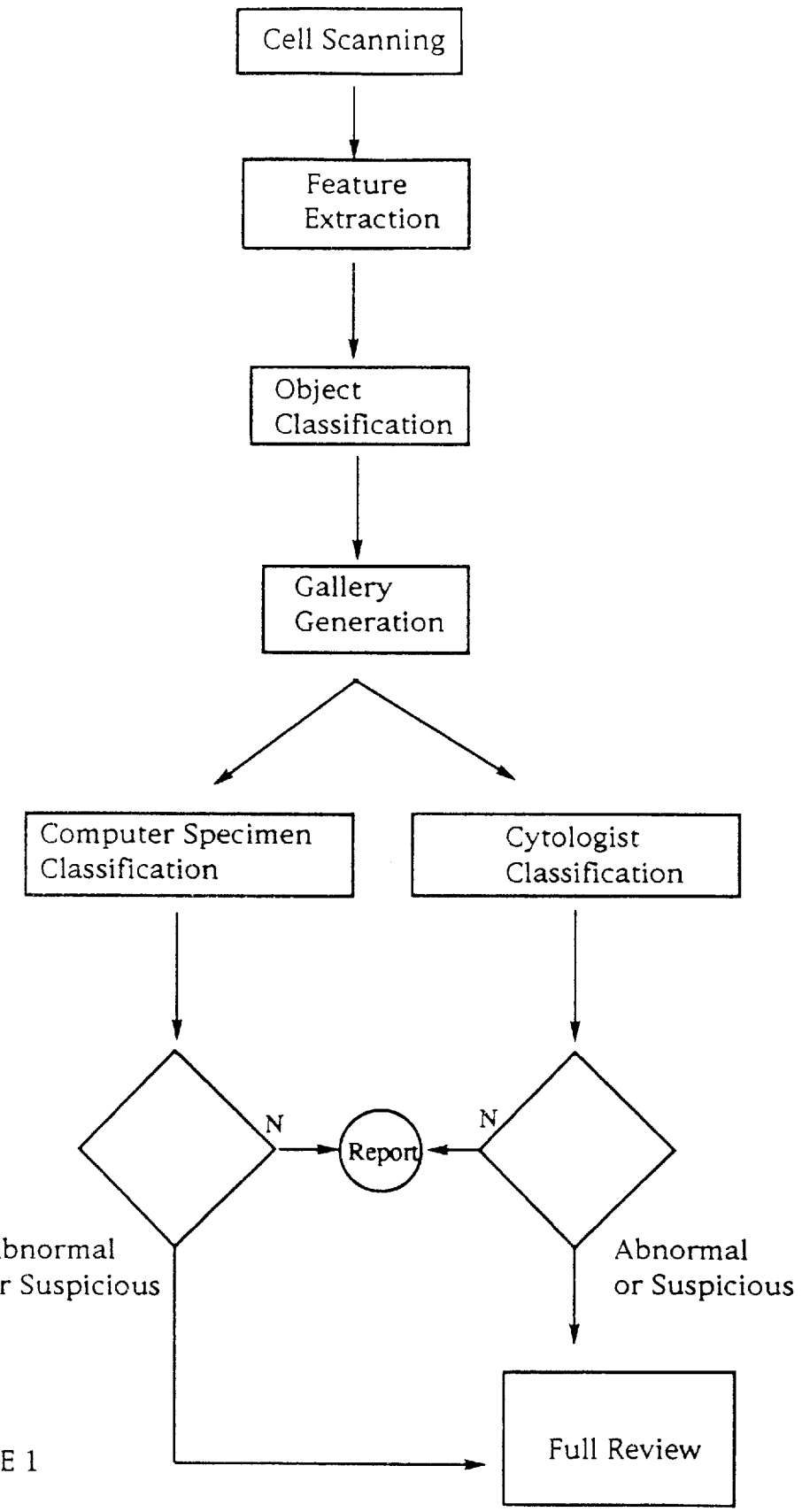
FIG. 1 is a flow chart depicting the interactive process of the subject invention.

Slides of cellular monolayers, prepared and stained in the manner described above, are introduced into the subject system. Referring to FIG. 1, slides are automatically scanned to identify objects on the slides and to classify the objects as to whether or not they are cells. Objects identified as cells are then classified into groups based on predetermined parameters. This is accomplished through a process of extensive feature extraction and analysis. The term "feature extraction" refers to identification of predetermined characteristics. The term "characteristics," in this context, refers to physically identifiable parameters, such as size (cellular, nuclear, etc.), shape, color, etc. Generally, features correspond to a cellular indicator. The term "cellular indicator" refers to a feature which is associated with a given cellular condition or event, such as binucleation within dividing cells.

The choice of features is determinable by one skilled in the art, based on the type of cells and conditions to be evaluated. For example, features used for cytology processes include, but are not limited to, the presence of more than one nucleus, increased nuclear size, and alterations in color, shape and size. The cell may be identified by color, shape, size, nuclear size, etc., or some combination of these characteristics. Abnormalities (deviant cellular indicators) may be determined based on the statistical analysis of cells having any given feature or group of features, for example, blue stained cells having a nuclear size greater than three micrometers and two nuclei.

The computerized system evaluates each object by assigning numerical values to each feature and then statistically manipulating the numerical values to generate a meaningful value. The term "meaningful value" refers to a number which indicates a particular cellular condition, for example, normal, atypical, low grade SIL, high grade SIL, malignant, etc. A compilation of the meaningful values allows the system to make a diagnosis based on the statistical analysis of occurrence for every cell of selected features. An important aspect of the invention is that the system's diagnosis should not be reported to the cytologist until after the cytologist has (i) reviewed a gallery of cells selected by the computer as most likely to exhibit the selected parameters and (ii) entered a cytologist's determination.

Prior to displaying a diagnosis, the system generates a gallery of cells which the system has determined most likely to exhibit the selected features. For example, in the case of cervical smears, the system scans for malignant cells, binucleated abnormal cells and heaps of abnormal cells, dysplastic cells, atypical cells, cells infected with HPV, endocervical cells and clusters of endocervical material. By finding endocervical cells within the sample, the cytologist is assured that the doctor has properly obtained the sample from the endocervical area. For Pap smear analysis, the gallery displays multiple cell types, because several types of cells are considered significant with respect to diagnosis.

Figure 5:
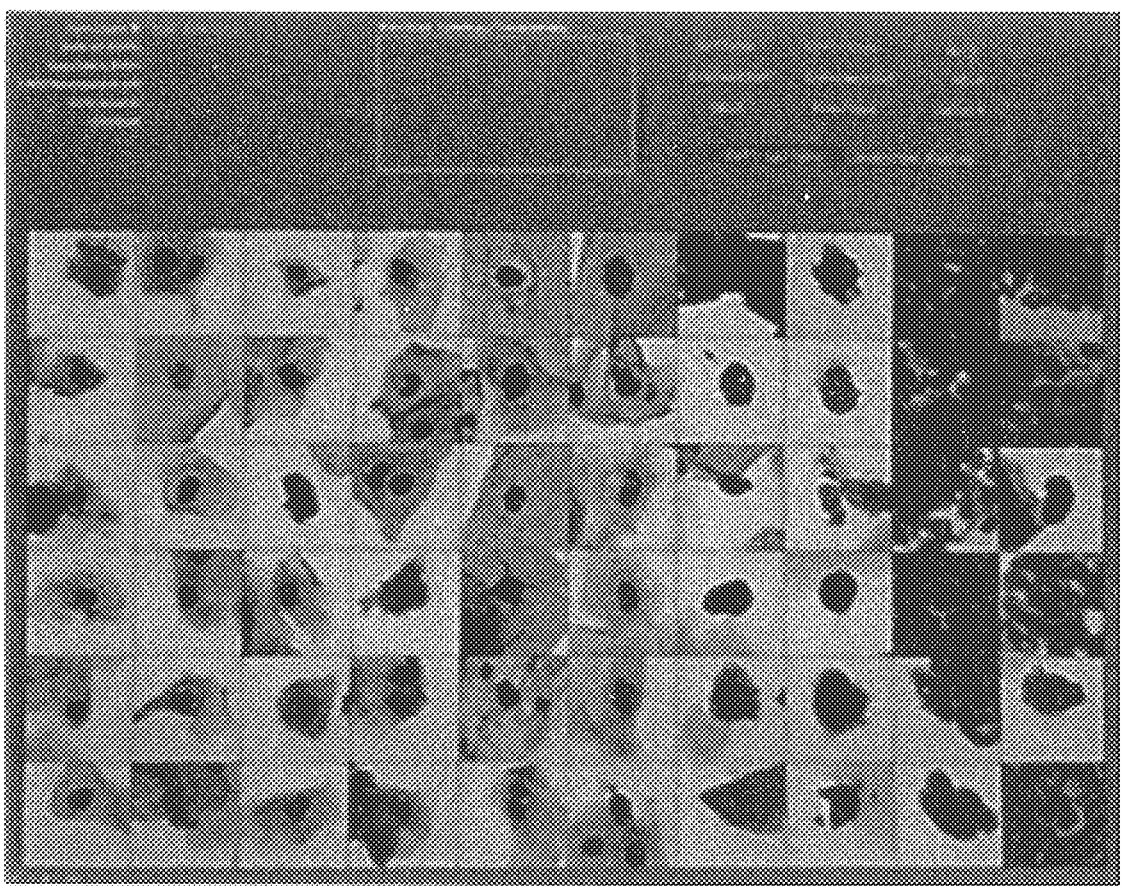
FIG. 5 is an illustration of a representative screen showing a gallery of cells as it would be presented to the operator.

Currently, the total number of cells displayed in the gallery is set to 120, in 8 categories (60 cells per television screen). However, gallery sizes that vary from about 16 to about 600 cells are preferred (about 8 to about 300 cells per television screen). Greater numbers of cells may be shown on large television screens, or by dividing the gallery into numerous screens. Any suitable display means may be used. However, it is currently preferred to use a television screen, more preferably a high definition television screen (HDTV). FIG. 5 depicts a television screen displaying a gallery of cells. The number of categories, number of cells, desired gallery size, etc. are preferably run-time selectable, to afford greater versatility.

The number of cells in each category is not strictly determined because not all slides contain each category of cells in sufficient quantity. This is especially true for benign slides which should contain no malignant, dysplastic, atypical or HPV infected cells. As this would lead to potentially empty categories, selection criteria are applied to the cells selected in the gallery creation module. Thus, for example, if 15 dysplastic are to be placed in the gallery (e.g. 15 cells per category and 8 categories total 120 images), and the computer was to find no cell which qualified as dysplastic, it would put in 15 cells which are closest to those showing dysplasia (oftentimes normal cells, especially in a normal sample).

The galleries may be arranged so that cells exhibiting the strongest feature responses are placed in a certain area of the television screen, such as on the left, and cells exhibiting the weakest feature responses are placed in a different area of the television screen, such as on the right. Thus, galleries may be arranged to show a gradient of cells ranging from those most clearly abnormal to those least abnormal. For example, in a category of 15 dysplastic cells, the three at the far left might be clearly dysplastic, the next three questionably dysplastic, and the remaining 9 cells normal. In such a situation, a cytologist would categorize the sample as dysplastic, because even one abnormal cell warrants such a finding. Numerous other presentation formats are also available.

The cytologist reviews the gallery of selected cells and makes an independent determination as to whether any of these cells are abnormal. At this point, the cytologist does not know the determination made by the system. It is only after the cytologist inputs a decision into the system (e.g., keys in the diagnosis) that the cytologist is shown the results of the computer analysis. As shown in FIG. 1, cytologist review and computer review are then compared. In other words, if computer and cytologist both believe the slide to show only normal cells, the slide receives no further processing, and the diagnosis "normal" is reported on the patient. If either the cytologist, computer, or both, find abnormalities, the slide is forwarded to another cytologist for a full review of the entire slide. "Full review" means a complete manual review of the slide by the cytologist, such as by using the cytology methods currently practiced in clinical laboratories throughout the world.

Figure 2:
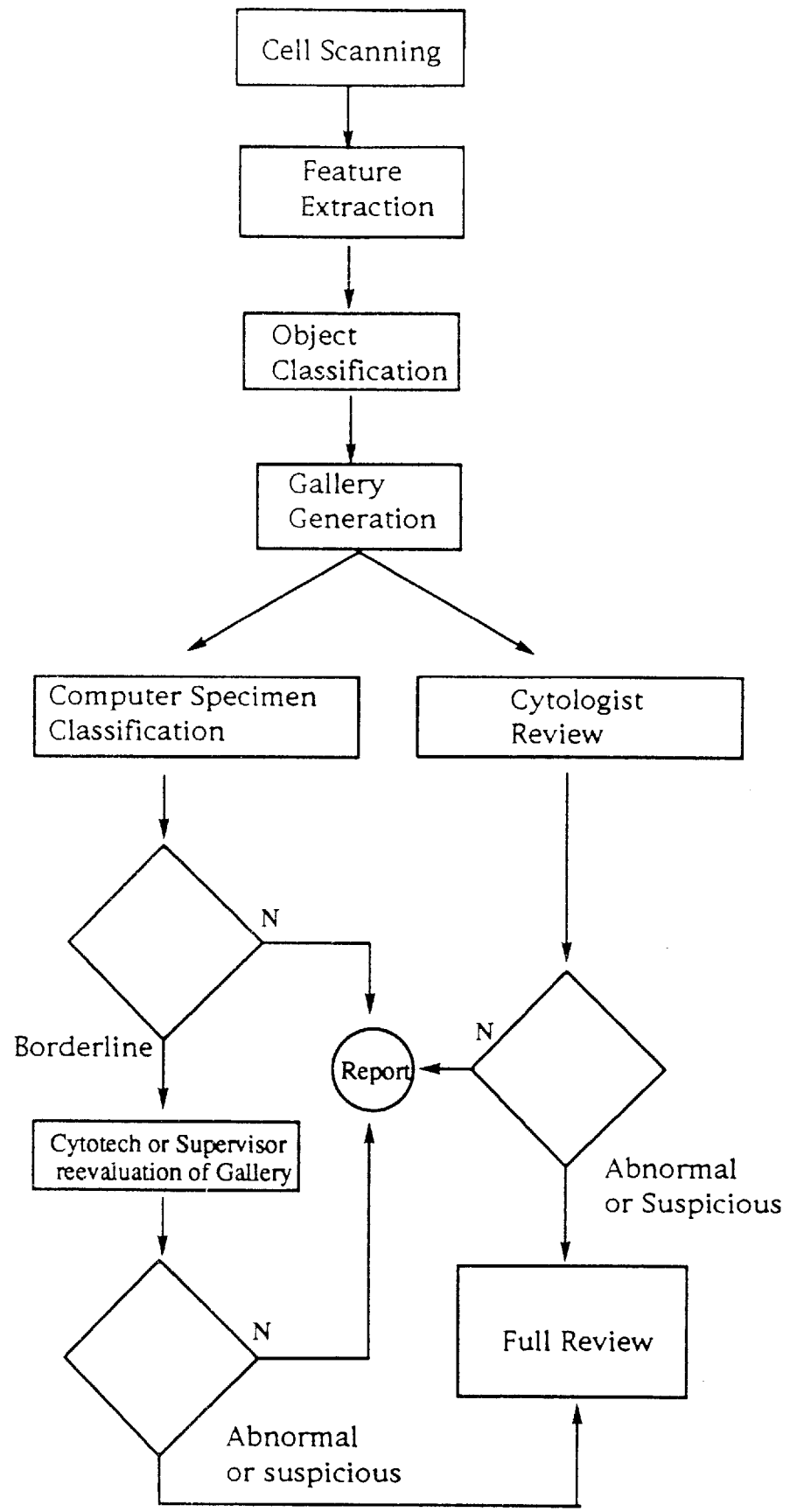
FIG. 2 is a flow chart depicting an alternative embodiment of the subject interactive process.

In the alternative embodiment depicted in FIG. 2, if the cytologist reviews the gallery and finds it to be normal, but the computer generates a questionable or borderline value, the gallery is shown to a supervisor who again reviews the gallery of cells. Another option would be for the cytologist to rereview the gallery himself. If the cytologist supervisor or the cytologist finds the gallery to be normal, the slide receives no further processing and a diagnosis of "normal" is reported. However, if the rereview finds any abnormal or questionable cells, the slide is subjected to full review.

EXAMPLES

The following section compares error rates obtained using the subject interactive system, cytologist review of a gallery of cells only and automated cytological machine review only. As it turns out, the subject interactive system significantly lowers the false negative rate while only marginally increasing the false positive rate.

Experimental Detail

Error rates (false negative and false positive) have been determined based on a sampling of 772 specimens. "False negative rate" as used herein denotes a test result that wrongly excludes an individual from a diagnostic category. "False positive rate" as used herein denotes a test result that wrongly assigns an individual to a diagnostic category. False negative rate is determined by dividing the number of false negative diagnoses by the number of false negative diagnoses plus the number of true positive diagnoses to obtain a quotient, which is then multiplied by 100. False positive rate is determined by dividing the number of false positive diagnoses by the number of false positive diagnoses plus the number of true negative diagnoses to obtain a quotient, which is then multiplied by 100.

The following error rates have been determined:

TABLE 1

| Reference Slide | Total Cases⁻ | cytotech review only | machine only (undecided = positive) | machine only (undecided = negative) | combined diagnosis |
|---|---|---|---|---|---|
| Normal | 228 | 37.3$^{a1**}$ | 33.4** | 14.5** | 44.3$^{a2**}$ |
| Abnormals | | | | | |
| atypical | 129 | 37.2$^{b1*}$ | 13.2* | 36.5* | 15.5$^{b2*}$ |
| low grade SIL | 129 | 10.9$^{c1*}$ | 10.1* | 24.8* | 2.3$^{c2*}$ |
| high grade SIL | 217 | 0.5* | 2.8* | 10.2* | 0.5* |
| malignant | 69 | 0.0* | 1.5* | 4.3* | 0.0* |

\* = False negative rate (FNR)
\*\* = False positive rate (FPR)
⁻ = The distribution of cases according to a concensus opinion of a panel of experts.
$a^1$, $a^2$, $b^1$, $b^2$, $c^1$ and $c^2$ are defined in the text.

For the purpose of comparing of the results obtained by the subject system with the results obtained by a cytologist, reference interpretations were generated for each monolayer sample. These reference interpretation were the culmination of extensive review by cytotechnologists and cytopathologists of both monolayer slides and conventional smears on the same patients. When available, biopsy data was also taken into consideration to derive the reference result. Thus, the reference interpretations represent the most reliable diagnosis, taking into account information beyond the slide itself.

The cytotech review column identifies the error rate obtained by a single cytologist reviewing the gallery of cells from the monolayer slide only. As shown in Table 1, gross abnormalities, such as malignancies, are very accurately detected by a cytotech alone reviewing a cell gallery (approximately 100% accuracy). By contrast, lesser abnormalities, such as atypical cells, are less accurately detected by a cytologist alone reviewing a cell gallery (approximately 62.8% accuracy).

The difference between the two machine only columns is due to the system classifying cases as positive, negative or undecided. The third column from the right considers undecided as positive, and the second column from the right considers undecided as negative. In clinical situations, both undecided and positive slides will require further review by a cytologist. The undecided=positive rates are computed with the assumption that the machine evaluation undecided is considered positive (this results in the lowest possible False Negative Rate and the highest False Positive Rate). The undecided=negative rates assuming all undecided cases are treated as negative.

Table 1 illustrates the effects of the integration of the machine decision (undecided=positive) with the cytotech's diagnosis:

False Positive Rate (FPR) increases from 37.3%$^{(a1)}$ to 44.3%$^{(a2)}$, or about 19%. An increase would be expected because of the strategy of accepting either the machine's or the cytotech's decision for abnormal as an abnormal diagnosis. Mathematically, this rate can only increase by the combination. However, it is unexpected that the increase is merely 19%, considering the following improvement in false negative rate.

False Negative Rates (FNR) for atypical and low grade SIL decrease significantly from 37.2%$^{(b1)}$ to 15.5%$^{(b2)}$ and from 10.9%$^{(c1)}$ to 2.3%$^{(c2)}$, a reduction by a factor of 4.7 (470% decrease). This indicates that the cell gallery, evaluated by a cytologist and the machine evaluation of the entire specimen are using different information from the slide. The decrease in error rate turned out to be unexpectedly remarkable.

The FNR for high grade SIL and malignancy did not change in this experiment. The 0.5% FNR for high grade SIL represent just one case out of the 217 scanned. The FNR for malignancy is already 0.0% by the cytologist review.

The total FNR joining all non-negative slides decreased from 11.6% by cytotech review to 4.4% when combining it with the machine evaluation. This is a 62% decrease on the False Negative Rate. At the same time the combination of cytologist review and machine evaluation increased the False Positive Rate only 7 percentage points or approximately 18.8%.

Although not wanting to be bound by theory, it is believed that the machine classification of the subject system is more sensitive to minor cellular changes than the cytologist. Thus, with the machine evaluation earlier detection may be possible, since these cells may show only very minor deviations from normal or malignancy associated changes. On the other hand, a single deviant cell would not cause the automated portion of the system to make a positive determination because of the statistical analysis employed. By contrast, a cytologist can make a determination based on a single abnormal cell. Thus, the combination of the automated system and cytologist synergistically increase the rate of detection.

Upon reading this specification, various alternative embodiments will become obvious to those skilled in the art. These embodiments are to be considered within the scope and spirit of the subject invention, which is only to be limited by the claims which follow and their equivalents. For example, even though the invention is primarily designed for cytological applications, it could be adapted for use in reviewing computer circuits, or other materials that can be optically scanned. Accordingly, the use of the subject method and system for. such application is to be considered within the spirit of the invention.

What is claimed is:

1. An interactive method for evaluating objects of interest in a sample using a computer-assisted system and an operator, which comprises the following steps performed in the order listed:

(a) the system scanning the sample using an automated scanning device and generating scan data corresponding to the sample;

(b) the system identifying the objects of interest from the scan data by comparing the scan data with previously inputted reference data corresponding to a first predetermined set of characteristics;

(c) the system generating a gallery of objects of interest selected from the identified objects of interest, the gallery including the objects of interest which exhibit the first predetermined set of characteristics;

(d) the system statistically analyzing occurrence of all objects of interest within the scan data and determining whether the statistical occurrence meets a predetermined threshold;

(e) the operator viewing the gallery to determine whether any of the objects of interest in the gallery exhibit a second predetermined set of characteristics without knowing the system's determination;

(f) the operator inputting into the system the determination of whether the objects of interest in the gallery exhibit the second predetermined set of characteristics;

(g) the system displaying to the operator the determination of whether the statistical occurrence of all objects of interest within the scan data meets the predetermined threshold; and (h) comparing the operator's determination with the system's determination, agreement indicating the given criterion has been met so as to achieve interaction of the evaluation.

2. The interactive method of claim 1, wherein the scanning comprises scanning a microscope slide.

3. The interactive method of claim 2, wherein the microscope slide contains cytological material.

4. The interactive method of claim 3, wherein the first predetermined set of characteristics correspond to physically identifiable parameters.

5. The interactive method of claim 4, wherein the physically identifiable set of parameters are selected from the group consisting of cell size, nuclear size, color and shape.

6. The interactive method of claim 1, wherein the generating of scan data comprises forming a digital image of the scanned sample.

7. The interactive method of claim 1, wherein the generating of the gallery further comprises displaying the gallery on a television screen.

8. The interactive method of claim 7, wherein the television screen is a high definition television screen.

9. The interactive method of claim 7, wherein the television screen displays about 60 cells at one time.

10. The interactive method of claim 1, wherein the first predetermined characteristic and the second predetermined characteristic are the same.

11. The interactive method of claim 1, wherein the computing of the occurrence of the objects of interest comprises assigning a value to each object of interest based on the number and nature of the characteristics identified from the first predetermined set of characteristics which are present on each object of interest.

12. The interactive method of claim 1, wherein the values assigned to the objects of interest are totaled and compared to a predetermined value, thereby determining whether occurrence meets the predetermined threshold.

13. The interactive method of claim 1, further comprising manually reviewing the slide if the operator's determination and the system's determination do not agree.

14. An interactive method for evaluating objects of interest in a sample using a computer-assisted system and an operator, which comprises the following steps performed in the order listed:

(a) the system scanning the sample using an automated scanning device and generating scan data corresponding to the sample;

(b) the system identifying the objects of interest from the scan data by comparing the scan data with previously inputted reference data corresponding to a first predetermined set of characteristics;

(c) the system generating a gallery of objects of interest selected from the identified objects of interest, the gallery including the objects of interest which exhibit the first predetermined set of characteristics;

(d) the operator viewing the gallery to determine whether any of the objects of interest in the gallery exhibit a second predetermined set of characteristics;

(e) the system statistically analyzing occurrence of all objects of interest within the scan data and determining whether the statistical occurrence meets a predetermined threshold;

(f) the operator inputting into the system the determination of whether the objects of interest in the gallery exhibit the second predetermined set of characteristics;

(g) the system displaying to the operator the determination of whether the statistical occurrence of all objects of interest within the scan data meets the predetermined threshold; and (h) comparing the operator's determination with the system's determination, agreement indicating the given criterion has been met so as to achieve interaction of the evaluation.

15. The interactive method of claim 14, wherein the scanning comprises scanning a microscope slide.

16. The interactive method of claim 15, wherein the microscope slide contains cytological material.

17. The interactive method of claim 16, wherein the first predetermined set of characteristics correspond to physically identifiable parameters.

18. The interactive method of claim 17, wherein the physically identifiable set of parameters are selected from the group consisting of cell size, nuclear size, color and shape.

19. The interactive method of claim 14, wherein the generating of scan data comprises forming a digital image of the scanned sample.

20. The interactive method of claim 14, wherein the generating of the gallery further comprises displaying the gallery on a television screen.

21. The interactive method of claim 20, wherein the television screen is a high definition television screen.

22. The interactive method of claim 20, wherein the television screen displays about 60 cells at one time.

23. The interactive method of claim 14, wherein the first predetermined characteristic and the second predetermined characteristic are the same.

24. The interactive method of claim 14, wherein the computing of the occurrence of the objects of interest comprises assigning a value to each object of interest based on the number and nature of the characteristics identified from the first predetermined set of characteristics which are present on each object of interest.

25. The interactive method of claim 14, wherein the values assigned to the objects of interest are totaled and compared to a predetermined value, thereby determining whether occurrence meets the predetermined threshold.

26. The interactive method of claim 14, further comprising manually reviewing the slide if the operator's determination and the system's determination do not agree.

27. An interactive method for evaluating objects of interest in a sample using a computer-assisted system and an operator, which comprises the following steps:

(a) the system scanning the sample using an automated scanning device and generating scan data corresponding to the sample;

(b) the system identifying the objects of interest from the scan data by comparing the scan data with previously inputted reference data corresponding to a first predetermined set of characteristics;

(c) the system generating a gallery of objects of interest selected from the identified objects of interest, the gallery including the objects of interest which exhibit the first predetermined set of characteristics;

(d) the system statistically analyzing occurrence of all objects of interest within the scan data;

(e) the system determining whether the statistical occurrence meets a predetermined threshold;

(f) the operator viewing the gallery of objects of interest;

(g) the operator determining whether any of the objects of interest in the gallery exhibit a second predetermined set of characteristics without knowing the system's determination, said operator determining step performed simultaneously with said system determining step;

(h) the operator inputting into the system the determination of whether the objects of interest in the gallery exhibit the second predetermined set of characteristics;

(i) the system displaying to the operator the determination of whether the statistical occurrence of all objects of interest within the scan data meets the predetermined threshold; and (j) comparing the operator's determination with the system's determination, agreement indicating the given criterion has been met so as to achieve interaction of the evaluation.

28. The interactive method of claim 27, wherein the scanning comprises scanning a microscope slide.

29. The interactive method of claim 28, wherein the microscope slide contains cytological material.

30. The interactive method of claim 29, wherein the first predetermined set of characteristics correspond to physically identifiable parameters.

31. The interactive method of claim 30, wherein the physically identifiable set of parameters are selected from the group consisting of cell size, nuclear size, color and shape.

32. The interactive method of claim 27, wherein the generating of scan data comprises forming a digital image of the scanned sample.

33. The interactive method of claim 27, wherein the generating of the gallery further comprises displaying the gallery on a television screen.

34. The interactive method of claim 33, wherein the television screen is a high definition television screen.

35. The interactive method of claim 33, wherein the television screen displays about 60 cells at one time.

36. The interactive method of claim 27, wherein the first predetermined characteristic and the second predetermined characteristic are the same.

37. The interactive method of claim 27, wherein the computing of the occurrence of the objects of interest comprises assigning a value to each object of interest based on the number and nature of the characteristics identified from the first predetermined set of characteristics which are present on each object of interest.

38. The interactive method of claim 27, wherein the values assigned to the objects of interest are totaled and compared to a predetermined value, thereby determining whether occurrence meets the predetermined threshold.

39. The interactive method of claim 27, further comprising manually reviewing the slide if the operator's determination and the system's determination do not agree.

40. A method for evaluating objects of interest in a sample using a computer-assisted system, which comprises the steps of:

(a) the system scanning the sample using an automated scanning device and generating scan data corresponding to the sample;

(b) the system identifying the objects of interest from the scan data by comparing the scan data with previously imputed reference data corresponding to a predetermined set of characteristics;

(c) a first evaluating of the objects of interest on the basis of cellular condition, said first evaluating step resulting in a first diagnosis;

(d) a second evaluating of the objects of interest on the basis of cellular condition, said second evaluating step resulting in a second diagnosis and performed independently of said first evaluating step and without knowledge of the first diagnosis.

41. A method according to claim 40, wherein the predetermined set of characteristics correspond to physically identifiable parameters.

42. A method according to claim 41, wherein the physically identifiable set of parameters are selected from the group consisting of cell size, nuclear size, color and shape.

43. The interactive method of claim 40, wherein the scanning comprises scanning a microscope slide.

44. The interactive method of claim 43, wherein the microscope slide contains cytological material.

45. The interactive method of claim 40, wherein the generating of scan data comprises forming a digital image of the scanned sample.

* * * * *